United States Patent [19]
Joslyn

[11] Patent Number: 4,812,292
[45] Date of Patent: Mar. 14, 1989

[54] CHEMICAL STERILANT RECOVERY AND CONVERSION

[75] Inventor: Larry Joslyn, Macedon, N.Y.

[73] Assignee: Joslyn Valve Corporation, Macedon, N.Y.

[21] Appl. No.: 112,334

[22] Filed: Oct. 26, 1987

[51] Int. Cl.[4] ...................... A61L 9/00; A01N 63/00; F28D 7/00; C07C 27/00
[52] U.S. Cl. .......................... 422/31; 422/2; 422/34; 422/235; 568/867
[58] Field of Search ...................... 568/867; 422/2, 31, 422/33, 34, 234, 235; 55/279

[56] References Cited

U.S. PATENT DOCUMENTS

| | | | |
|---|---|---|---|
| 3,922,314 | 11/1975 | Cocuzza et al. | 568/623 |
| 3,970,711 | 7/1976 | Reiche et al. | 568/867 |
| 4,113,438 | 9/1978 | Brooks et al. | 422/235 |
| 4,169,010 | 9/1979 | Marwill | 435/247 |
| 4,349,417 | 9/1982 | Rebsdat et al. | 568/867 |
| 4,508,927 | 4/1985 | Bhise et al. | 568/858 |

Primary Examiner—Barry S. Richman
Assistant Examiner—Lyle Alfandary-Alexander
Attorney, Agent, or Firm—Martin Lukacher

[57] ABSTRACT

Chemical sterilants such as ethylene oxide are recovered from sterilization processes and converted into safer chemical compounds by non-catalytic hydrolysis.

7 Claims, 1 Drawing Sheet

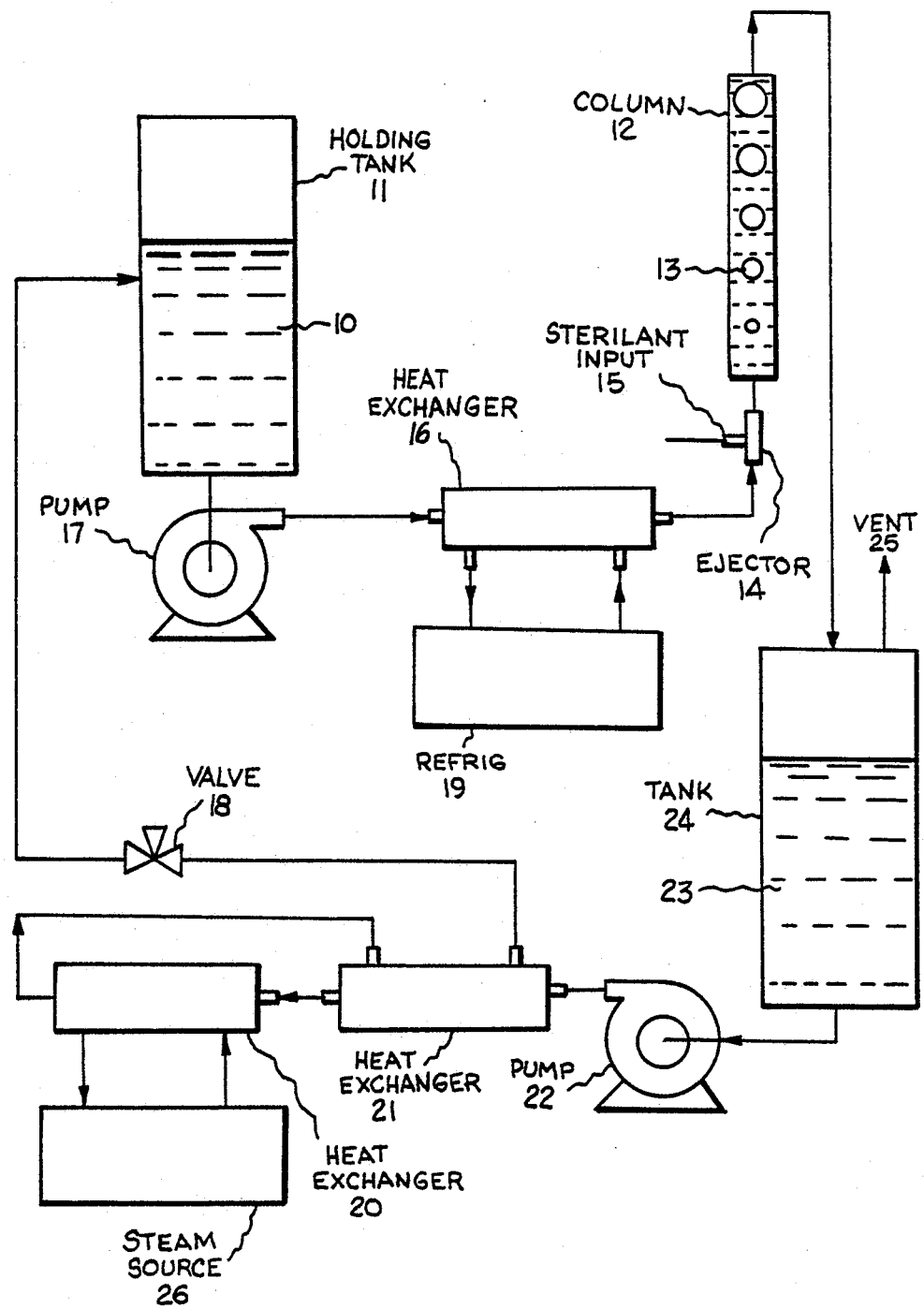

4,812,292

CHEMICAL STERILANT RECOVERY AND CONVERSION

FIELD OF THE INVENTION

This invention relates to the recovery of chemical sterilants and more particularly, to the recovery of gaseous toxic sterilants such as ethylene oxide and their conversion to useful and safer compounds.

BACKGROUND OF THE INVENTION

Gaseous chemical sterilants, such as ethylene oxide, are widely used for sterilizing various plastic, fabric and metal articles in sterilizing chambers. However, the dumping of these sterilants into the environment from sterilizers has been a problem for years. The sterilant may be blown toward inhabited areas resulting in persons being exposed to toxic chemicals. Some sterilants, such as ethylene oxide, can be hydrolyzed into a safer usable byproduct such as ethylene glycol. Systems are available to scrub ethylene oxide from a sterilizer discharge effluent and convert it to ethylene glycol. These systems, however, use sulfuric acid as a catalyst for hydrolysis. This technology has several disadvantages.

Sulfuric acid solutions at the required concentration for hydrolysis are hazardous to handle. In some systems the acid solution is pumped into spray nozzles at relatively high pressures and a piping failure can result in injury to personnel. In other systems the sterilant is bubbled through the acid in plastic tanks. At high flow rates the pressure can rupture the tanks. A leak in the holding tanks due to high pressure or mechanical failure can be hazardous to clean up and can damage other equipment.

Periodically, the acid scrubber liquid has to be changed as the efficiency of the system decreases. The acid solution has to be neutralized for waste disposal, usually with caustic sodium hydroxide. This introduces a further hazard. In addition, the glycol to be collected for reuse is contaminated with sodium sulfate.

The efficiency of acid scrubber systems changes with the temperature of the acid solution and the concentration of ethylene glycol which forms in the solution. The capture efficiency of the systems decreases as the ethylene glycol content or the temperature of the solution increases. If the temperature decreases, however, the rate of hydrolysis decreases. Heating and cooling of the acid solution for a more controlled capture efficiency and subsequent hydrolysis are difficult and costly.

SUMMARY OF THE INVENTION

The present invention provides an improved method for recovering ethylene oxide or other chemical sterilants, such as propylene oxide, which are discharged from a sterilizer, and converting such sterilants into glycols or other safe to handle compounds without chemical additives. This produces high purity byproducts such as ethylene glycol which can be economically reused. Additionally, this new method requires no added catalysts or other hazardous chemicals.

In the method of the invention a hydrolyzable sterilant gas is recovered as a useful aqueous solution of hydrolysate. The method comprises cooling an aqueous liquid stream to a temperature at which the hydrolyzable gas is highly soluble in the liquid, mixing the cooled liquid stream with a stream of the hydrolyzable sterilant gas, and subjecting the resulting stream to a temperature and pressure causing hydrolysis of the dissolved sterilant and for a sufficient time to hydrolyze substantially all of the sterilant. The resulting hydrolysate is cooled and recycled. In a preferred embodiment the sterilant is ethylene oxide and the cooled solution of ethylene oxide is preheated by indirect heat exchange with the heated hydrolyzed solution containing ethylene glycol.

Other objects, feauures and advantages of the invention will become more apparent from a reading of the following description detailing the method of the invention and the presently preferred apparatus for carrying out the method as shown in the accompanying drawings, in which the sole figure is a schematic representation of such apparatus.

BRIEF DESCRIPTION OF THE DRAWING

The FIGURE shows the element of the combination.

DETAILED DESCRIPTION OF THE INVENTION

Referring to the drawing, the emission recovery apparatus comprises a liquid holding tank 11 which contains water or an aqueous solution of glycol 10. The holding tank is connected to a liquid pump 17. The liquid pump feeds the water or solution through a heat exchanger 16 which is cooled by a refrigeration system 19. After being cooled to a predetermined temperature e.g. to less than 33° F. when the sterilant gas is ethylene oxide, the water is passed through Venturi mixer or ejector 14. The ejector mixes the water with ethylene oxide or other hydrolyzable sterilant from the sterilizer (not shown). The sterilant is fed into the ejector input port 15. Because of the very cold water temperature, water soluble sterilants or sterilants which are condensable at the cold temperatures enter into solution with the water. The non-condensable gases, e.g., air, and the water/sterilant solution are fed through a column 12 to allow time for the sterilant to go into solution after being mixed with the water. The remaining non-condensable gases, shown as bubbles 13 in column 12, and the water/sterilant solution are discharged into a holding tank 24. The gases and the liquid are separated in the holding tank such that the liquid is collected as shown at 23 and the gases are vented to atmosphere through a vent conduit 25.

The water/sterilant solution 23 is fed through a preheat heat exchanger 21 by means of a high pressure liquid pump 22. The discharge from heat exchanger 21 at a temperature, e.g., of 100° F., is fed into a higher temperature, second heat exchanger 20 which is heated by steam or other heating means 26 to a temperature, e.g., of 300° F. The discharge of the second heat exchanger is fed back through the first heat exchanger 21 and then through a spring loaded relief valve 18 to the original holding tank 11. The two heat exchangers 21 and 20 are used to heat the solution 23 to an elevated temperature such as 300° F., to accelerate hydrolysis. The hot stream discharged from the second heat exchanger 20 is fed into the first heat exchanger 21 for indirect heat exchange with the chilled ethylene oxide solution 23 from tank 24 to cool the hydrolyzed solution from exchanger 20 before it is discharged into the holding tank 11 and also to conserve energy by preheating the solution 23. The spring loaded relief valve 18 is adjusted to a pressure at which the sterilant and the water solution remain in the liquid state at the temperature developed in the heat exchangers 21 and 20. For example, at 300° F. the pressure on the pressure relief valve is set at 100 psig in order to maintain the solution in the liquid state. At this temperature, the time required for substantially complete hydrolysis of the ethylene oxide to ethylene glycol in the absence of added catalysts is about one hour. At higher temperatures the residence time for completion of hydrolysis can be shorter. Thus the pump 22 flow rate and the heat exchangers 20 and 21 have to be sized such that hydrolysis is substantially complete in the absence of added catalysts before the stream is discharged into the holding tank 11.

As the process proceeds, the liquid in the holding tank 11 changes gradually from water to an aqueous solution of ethylene glycol as the process proceeds. Because of this, the allowable temperature of the solution 10 can be reduced in the heat exchanger 16 to below the freezing point of water as the glycol content increases. Further cooling of the solution with the refrigeration means 19 and heat exchanger 16 before the mixing action in the ejector 14 and subsequent discharge in the holding tank 24 provides further reduction of the partial pressure of sterilant gas in the gases discharged to the atmosphere through conduit 25. The increase in efficiency allows nearly 99.7% of the sterilant to be captured from sterilant mixtures of ethylene oxide and Freon (dichlorodiflouromethane) gas. As the process continues the concentration of ethylene glycol in the solution 10 increases. When the concentration increases to 60% or above, the ethylene glycol is economically usable. Because there are no additives to the water solution, a high grade ethylene glycol solution collects in tank 11, requiring no further processing as would be required with acid scrubber systems. It should be appreciated that the same kind of hydrolysis reaction occurs with other hydrolyzable chemical sterilants. For example, when the sterilant is propylene oxide the resultant product is propylene glycol. Although the reaction of water with an alkylene oxide to form a glycol, e.g. ethylene oxide reacting with water to form ethylene glycol, is commonly in this art referred to as hydrolysis, as it is herein, the reaction is also sometimes called hydration.

Variations and modifications in the herein described preferred embodiments of the invention within the scope of the invention will suggest themselves to those skilled in the art. Accordingly, the foregoing description should be taken as illustrative and not by way of limitation.

I claim:

1. In a process for sterilizing articles by contacting said article with an alkoxide sterilant gas and subsequently recovering said alkoxide gas from the sterilization process, the improvement wherein said recovery step comprises:

(a) cooling an aqueous liquid stream at which the alkoxide sterilant gas is highly soluble in the liquid of the stream;
   (b) mixing the liquid stream cooled during said cooling step with a second stream of alkoxide sterilant gas to provide a resulting solution in an aqueous third stream of said gas dissolved in the liquid of said first named aqueous stream;
   (c) subjecting the third aqueous stream containing said alkoxide sterilant gas dissolved therein to conditions of temperature and pressure causing hydrolysis of said dissolved sterilant and for a period of time sufficient to hydrolyze substantially all of the dissolved sterilant and provide an aqueous solution of hydrolysate; and
   (d) recycling said aqueous solution of hydrolysate as said first named liquid stream to said cooling step.

2. The method of claim 1 wherein the improvement further comprises the step of cooling said aqueous solution of hydrolysate by heat exchange with said third stream.

3. A method accordirg to claim 1 wherein the sterilant gas is ethylene oxide.

4. The method according to claim 3 the improvement further comprises wherein said mixing step being carried out by injecting said second stream of ethylene oxide gas into said first aqueous stream which is a chilled stream of water or of an aqueous ethylene glycol solution obtained from said recycling step; separating from said third stream non-condensable gases; and said subjecting step is carried out by preheating said third stream from which said non-condensing gases are separated by heat exchange with a hot stream of ethylene glycol solution; further heating said preheated third stream to hydrolysis temperature to hydrolyze ethylene oxide to ethylene glycol in said hydrolysate; and cooling said hydrolysate; and further comprising the step of collecting said aqueous solution of hydrolysate after cooling in said subjecting step as ethylene glycol solution.

5. The method according to claim 4 wherein the improvement further comprises said aqueous solution of hydrolysate being collected in a tank, and said recycling step comprises the step of pumping said solution from said tank to provide said first liquid stream.

6. The method according to claim 3 wherein the improvement further comprises being said subjecting step carried out by heating to said hydrolysis temperature in the absence of added catalysts for a sufficient time and at a sufficient temperature for substantially all of the ethylene oxide to be hydrolyzed to ethylene glycol.

7. The method according to claim 6 wherein the improvement further comprises the step of circulating said hydrolysate as said hot stream of ethylene glycol solution in heat exchange relationship with the solution resulting from said separating step to carry out said preheating step.

* * * * *